(12) United States Patent
Garvey et al.

(10) Patent No.: US 8,840,842 B2
(45) Date of Patent: Sep. 23, 2014

(54) DECONTAMINATION SYSTEMS AND METHODS OF USE THEREOF

(75) Inventors: James F. Garvey, Williamsville, NY (US); John A. Lordi, Williamsville, NY (US); James Wulf, Williamsville, NY (US)

(73) Assignee: Buffalo BioBlower Technologies, LLC, Buffalo, NY (US)

( * ) Notice: Subject to any disclaimer, the term of this patent is extended or adjusted under 35 U.S.C. 154(b) by 769 days.

(21) Appl. No.: 12/860,425

(22) Filed: Aug. 20, 2010

(65) Prior Publication Data

US 2010/0316535 A1 Dec. 16, 2010

Related U.S. Application Data

(62) Division of application No. 12/122,536, filed on May 16, 2008, now Pat. No. 7,799,272.

(60) Provisional application No. 60/938,353, filed on May 16, 2007.

(51) Int. Cl.
*A61L 9/16* (2006.01)

(52) U.S. Cl.
CPC .................................. *A61L 9/16* (2013.01)
USPC .................................. 422/125; 422/120

(58) Field of Classification Search
CPC .......................................................... A61L 9/16
USPC ................................................. 422/33, 120, 125
See application file for complete search history.

(56) References Cited

U.S. PATENT DOCUMENTS

| | | | |
|---|---|---|---|
| 3,055,644 A * | 9/1962 | Wennerberg | 165/66 |
| 5,846,066 A | 12/1998 | Troup | |
| 6,402,812 B1 * | 6/2002 | Perrotta et al. | 95/95 |
| 7,125,439 B2 | 10/2006 | Bennett | |
| 2004/0184907 A1 * | 9/2004 | Garvey et al. | 415/1 |
| 2006/0226081 A1 | 10/2006 | Lupton et al. | |

* cited by examiner

*Primary Examiner* — Sean E Conley
(74) *Attorney, Agent, or Firm* — Woods Oviatt Gilman LLP; Katherine H. McGuire, Esq.

(57) ABSTRACT

A system for reducing biological and/or chemical contaminants within a feed fluid stream includes in one embodiment at least one recuperator having a cold pass and a hot pass, wherein a contaminated fluid stream is introduced into the cold pass of the recuperator; optionally heating the feed fluid stream using a heater; and introducing the feed fluid stream into a compressor, and compressing the fluid stream to an elevated pressure, resulting in heating of the fluid stream to an elevated temperature, thereby producing a decontaminated fluid stream.

18 Claims, 4 Drawing Sheets

DECONTAMINATION SYSTEMS AND METHODS OF USE THEREOF

CROSS-REFERENCE TO RELATED APPLICATION

Figure 1:
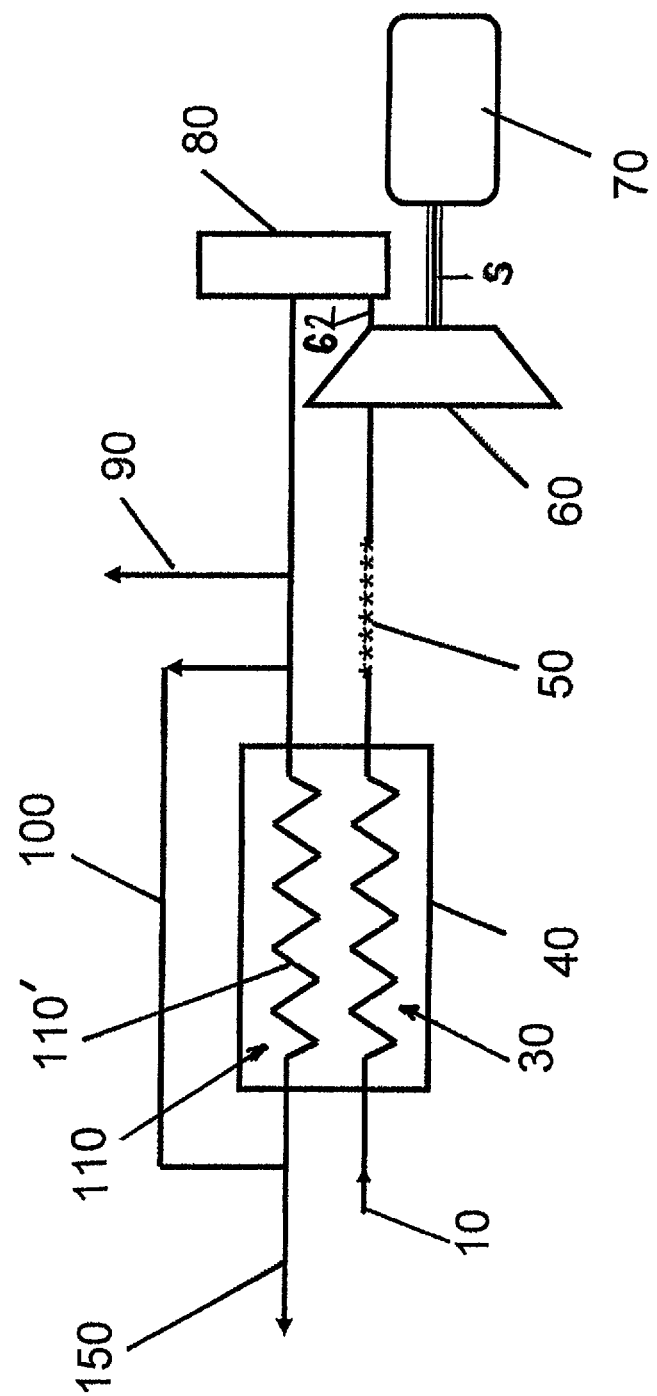

This is a divisional application of U.S. patent application Ser. No. 12/122,536, filed May 16, 2008, which in turn claims the benefit of priority from Provisional Application Ser. No. 60/938,353, filed May 16, 2007, the disclosure of which is incorporated herein by reference, and application Ser. No. 12/035,418 filed Feb. 21, 2008, which is a continuation of application Ser. No. 10/765,807 filed Jan. 27, 2004, now U.S. Pat. No. 7,335,333, which in turn claims the benefit of Provisional Application Ser. No. 60/486,507 filed Jul. 11, 2003 and Provisional Application Ser. No. 60/445,979 filed Feb. 7, 2003.

BACKGROUND OF THE INVENTION

The present invention relates to the destruction of contaminants entrained in a fluid stream, particularly to the destruction of non-biological particulate matter or biological contaminants such as spores, bacteria or viruses entrained in this fluid stream, particularly in a gas stream such as contaminated air. As used herein the term "destroy" broadly means killing or otherwise converting all or some of the contaminants within the fluid to a state which is less harmful to humans, animals or other organisms or devices present in environments requiring or benefited by a purified fluid. The present invention also is directed to destroying or altering chemical species which are entrained in a fluid stream, and particularly a contaminated air stream. As used herein the term "alter" broadly means any change in the chemical structure which results in the chemical being less harmful to humans, animals or other organisms or devices present in environments requiring or benefited by a purified fluid. In one aspect, the present invention is directed to destruction or altering of biological and/or chemical contaminants (sometimes referred to herein as "agents") as occurs by passage of the fluid stream through a compressor, for example a Roots-type or positive-displacement compressor, a centrifugal or high pressure fan centrifugal compressor, etc. In a particularly contemplated embodiment of the present invention, some of the heat imparted to the fluid stream during passage through the compressor is recovered from the fluid stream outflow downstream of the compressor and fed back to add heat to the compressor, thereby reducing the energy requirements for destruction of agents or chemical species through the compressor, as well as optionally producing a final fluid stream temperature more closely matching human and/or machine-tolerable temperatures, ambient temperatures, or the like, if needed for the particular application.

In the world today pathogens, viruses, bacteria and chemical species in the air either naturally or deliberately placed there are becoming an increasing health risk. Many bacteria are developing resistance to antibiotics and fewer new antibiotics are being developed. Outbreaks of airborne infections have been reported in hospitals. Clearly a better way of dealing with this health threat is needed. Terrorists have used bacteria and chemical species in attacks. Anthrax contaminated a U.S. Capital office building. The defense today against these species is typically HEPA filters capable of trapping particles as small as 0.3 microns. However, HEPA filters must be changed frequently, and used HEPA filter materials in some cases must be treated as hazardous waste. Furthermore, the performance of HEPA filters is dependent on their installation, and on the care taken in their replacement. Thus, for example, poor installation can result in the passage through the filtering system of unfiltered air, defeating the purpose of the filtration system and, in a worst-case scenario, leading to human sickness or death from contaminated air, e.g., air contaminated by biohazardous agents or chemical agents.

As an alternative to HEPA filtration, biological and/or chemical agents may be destroyed or altered rather than removed by filtration. In this regard, studies have shown some bacteria species can be destroyed at temperatures as low as 100° C. At temperatures approaching 250° C. almost all pathogens, viruses and bacteria are destroyed. At somewhat even higher temperatures, chemical species are destroyed or altered by thermal decomposition processes. Thus, sufficiently high temperatures may be used to destroy and/or alter biological and/or chemical agents.

While high temperatures may be used to destroy or alter such biological and/or chemical agents as described above, the method or system by which such high temperatures are generated is of utmost importance. Such heating methods and systems are useless unless they can demonstrate commercial viability. Thus, if the heating method or system has high power consumption and/or inordinately long processing times (i.e., time of exposure of the fluid stream to the high temperature), the method/system would simply not be commercially viable.

One possible method for high temperature destruction or altering of biological and/or chemical agents in a fluid stream is by passage of a fluid stream through, e.g., a positive-displacement compressor such as a Roots-type compressor as is described in U.S. Pat. No. 7,335,333, the disclosure of which is incorporated herein by reference, wherein it is disclosed how such passage through the compressor destroys bacteria, bacterial spores, and other biological agents in the fluid stream. As disclosed in the '333 patent, upwards of 99.9% of *Bacillus glonigii* (Bg) spores, an anthrax stimulant, where killed by compressive heating to about 200° C. in a single pass through a Roots-type positive displacement compressor.

Although methods based on passage of a fluid stream through a positive displacement compressor such as a Roots-type compressor as described in the '333 patent are desirable for the reasons set forth above, it would be advantageous to further improve the energy efficiency of these methods. For example, it would be particularly advantageous to use some of the heat contained in the fluid stream at the outflow end of the positive-displacement compressor or downstream of the positive-displacement compressor to lower the energy costs of operating the compressor. For example, recovery of some of the heat of the fluid in the outflow stream could be redirected back to the compressor (e.g., to heat the compressor body itself and/or the inlet fluid to the compressor, etc), thereby lowering the amount of additional heat required to be generated by the compressor to obtain the necessary kill/decontamination conditions in the compressor. Such methods would have an additional energy benefit of reducing the energy requirements for lowering the temperature of the output fluid stream to a range suitable for exposure to humans, machinery, or other end uses, as required. In the absence of removal of heat from the sterilized heated fluid outflow stream, depending on the application, this stream must be cooled prior to its introduction into spaces occupied by, e.g., humans, animals or other organisms or devices as discussed above. By directly removing some of the heat from this fluid output flow stream, energy input that would otherwise be required to cool this stream may thus be avoided.

There therefore exists a need for improved, energy-efficient methods and systems for destroying or altering biological and/or chemical agents in a fluid stream.

SUMMARY OF THE INVENTION

The present invention successfully address the above-identified needs. In one aspect, the present invention is directed to reducing the energy costs of destroying or altering targeted biological and/or chemical agents in a fluid stream. The term "targeted" is used herein to indicate certain applications may require destruction of only one or possibly several particular types of agents (e.g., mold spores) and the operating requirements of the system may therefore be set and optimized accordingly. In one possible embodiment, the present invention provides an energy-efficient method for reducing or substantially eliminating targeted biological and/or chemical agents within a fluid stream, comprising the steps of: a) introducing the fluid stream into a cold pass of at least one recuperator; b) optionally heating the fluid stream exiting the recuperator using a heater; c) introducing and compressing the fluid stream in a compressor, resulting in the pressurization and heating of the fluid stream to an elevated temperature; d) venting a portion of the compressed and heated fluid stream; e) bypassing a first portion of the compressed and heated fluid stream around a hot pass of the recuperator; f) passing a second portion of the compressed and heated fluid stream through the hot pass of the recuperator; and g) recombining the first and second flow portions of the fluid stream, thereby producing a decontaminated fluid stream. The design and operation of recuperators are discussed in "Compact Heat Exchangers", 3rd Edition, W. M. Kayes and A. L. London, McGraw-Hill, 1984.

BRIEF DESCRIPTION OF THE DRAWINGS

FIG. 1 provides a schematic illustration of one embodiment of the decontamination system of the present invention wherein the treated feed fluid may be at a temperature above the ambient system inlet temperature;

FIG. 2 provides a schematic illustration of one embodiment of the decontamination system of the present invention where compression, heat exchange and expansion stages are used to cool the decontaminated fluid stream obtained from a recuperator; and FIGS. 3 and 4 provide schematic illustrations of two embodiments of the decontamination system of the present invention that use stages of compression, expansion and heat exchange, when the treated fluid steam is required to be delivered above, below, or at the ambient system inlet temperature

DETAILED DESCRIPTION OF THE INVENTION

The term "contaminant" or "contamination" or "agent" as used herein refers to undesirable particulate matter (living or not), biological agents such as a viruses, fungi, molds, spores, bacteria, etc., or unwanted or dangerous chemical species entrained within a fluid flow.

"Fluid" as used herein refers to the fluid passing through the system of components of the present invention, including but not limited to the systems of the present invention shown in the accompanying figures. "Fluid" includes liquids and gases, and preferentially refers to gases such as air contaminated by biological and/or chemical agents. However the present invention is also directed to liquids, including, for example, water from a municipal or other water supply that is contaminated by biological and/or chemical agents.

FIG. 1 shows one embodiment of the present invention. In FIG. 1, feed fluid 10 first flows through a cold pass 30 of recuperator 40. As described further below, once the system is operational and begins providing an output flow, during passage through cold pass 30, the feed fluid temperature is increased by transfer of heat from the heated fluid flow 110' passing through the hot pass 110 of recuperator 40. In this embodiment, feed fluid 10 enters cold pass 30 at the pressure of the source from which it is taken, for example, sources such as an open or enclosed and/or environmentally-conditioned space, a piping or duct system, or a pressure vessel. Thus, once heated fluid flow 110' begins passing through hot pass 110, feed fluid 10 begins increasing in temperature as it flows through cold pass 30 of recuperator 40. In the preferred embodiment, recuperator 40 is a counter-flow recuperator.

After passage through cold pass 30 of recuperator 40, feed fluid 10 may be further heated by passing through optional heater 50, which may be powered by any appropriate source such as electricity or fuel combustion, for example. Although all the drawings provided herein show heater 50 as a standard component of the system of the present invention, it may be dispensed with in some contemplated embodiments of the invention. In general, however, the presence of heater 50 is preferred, as it allows for the fluid stream flowing through the system to be heated more quickly to a sufficiently high temperature, preferably about 200° C. to about 300° C., to achieve destruction and/or alteration of some or substantially all targeted biologic and/or chemical agents in the fluid stream.

Thus, for example, heater 50 can be operated as the system starts up, enabling treatment temperature to be reached in less time than the system without heater 50. Additionally, heater 50 may be operated continuously or intermittently during steady state operation of the system in order to achieve other advantageous effects.

Feed fluid 10 next passes from heater 50 to a compressor 60 which can be driven by electrical motor 70 or any other appropriate power source. Compressor 60 may be any suitable compressor for the particular application such as a centrifugal or high fan centrifugal compressor, or a Roots-type compressor, such as the positive-displacement or Roots-type compressors operated as described in the previously mentioned U.S. Pat. No. 7,335,333.

Passage of feed fluid 10 through compressor 60 results in elevation of the feed fluid temperature to treatment conditions. The heated fluid is preferably discharged from compressor 60 as indicated by line 62 into a residence chamber 80 which allows the heated fluid stream to remain at treatment temperature for a period of time sufficient to allow a substantially complete destruction and/or alteration of undesirable biologics and/or chemical species. Although residence chamber 80 is preferred, in other aspects of the present invention it may be dispensed with altogether, or it may be replaced or supplemented with other devices such as, for example, a catalytic converter vessel containing a catalyst that promotes destruction and/or alteration of targeted biological and/or chemical species more quickly and/or at a lower temperature. Even in the absence of a residence chamber, it is of course understood that as the fluid flows through conduit from compressor 60 through and out recuperator 40, the flow is, in effect, in dwell time, i.e., time at elevated temperature prior to release from the system into the surrounding space.

When residence chamber 80 is employed in the method of the present invention, the residence time of the fluid to be treated in residence chamber 80 is determined as that amount of time required to destroy and/or alter the desired amount of targeted agents. The volume of fluid being treated as well as the types of agents being targeted for destruction and/or alteration are of course factors that will help determine the required dwell time. For example, the minimum residence time in chamber 80 may be determined and optimized by testing whether or not substantially all harmful agents in the fluid contained in residence chamber 80 have been destroyed and/or altered. Such determination may be made by, for example, withdrawing a fluid sample from residence chamber 80, e.g., by use of an outlet port (not shown) of residence chamber 80, and measuring biological and/or chemical contaminant levels in the sample. Alternatively or in addition to sampling, biological and/or chemical sensors may be placed within residence chamber 80 such that the levels of these materials may be continuously or periodically tested during residence of the fluid within residence chamber 80. Such sensors are described in, for example, the previously mentioned U.S. Pat. No. 7,335,333, and are also commercially available for various types of biological and/or chemical agents.

Following passage through residence chamber 80, FIG. 1 shows the fluid flow as divided into: 1) a first flow portion 100 that bypasses recuperator 40; 2) a second flow portion that passes through the hot pass 110 of recuperator 40 and is recombined with first portion 100; and 3) optionally, a third flow portion 90 that may be vented from the system. Although this arrangement is preferred because it allows for enhanced control of the temperature of the leaving stream 150 downstream of recuperator 40, other contemplated embodiments include only recuperator 40 (i.e., without dividing and/or recombining of the fluid stream from compressor 60 or optional chamber 80), as well as recuperator 40 in combination with either (but not necessarily both) of the other two fluid flow streams, i.e., first portion 100 or third portion 90. It is understood that fluid flows through the system are provided via appropriate conduit. Additionally, variations in fluid flow volume and/or rate through these first, second, and/or third portions may be obtained by introducing into the fluid flow control conduit of the system of the present invention appropriate fluid control devices, i.e., petcocks, valves, etc., to redirect fluid flow through one or more of these three portions as appropriate. Although such fluid flow devices are not shown in the drawings, they are well-known to the skilled artisan.

As discussed above, fluid flow may be directed through the three portions shown in FIG. 1 in order to selectively vary the temperature of leaving stream 150, as well as to obtain other desirable properties for the system of the present invention. Thus, for example, an increase of third flow portion 90 can increase the effectiveness of recuperator 40 by removing energy from the system and thereby even further lowering the temperature of the flow leaving hot pass 110 of recuperator 40. First flow portion 100, which bypasses hot pass 110 of recuperator 40, can serve to allow the temperature of the treated fluid to be increased when heating is required in the decontaminated stream. Finally, the third flow portion 110' that passes through hot pass 110 of recuperator 40 is used to decrease the temperature of leaving stream 150 by transfer of heat to cold pass 30 and stream 10 flowing therethrough.

Specifically, with regard to venting from the system of the third flow portion 90, such venting provides a lower mass flow in hot pass 110 than in cold pass 30 of recuperator 40, thereby increasing recuperator effectiveness and lowering leaving air temperature of stream 150. The vented mass flow may be selected to be that amount of flow volume required to remove the heat of compression imparted by the compressor 60 that is not otherwise lost through heat leaks from the system components and piping. The amount of venting may be varied according to the amount of cooling of the output flow 150 as desired or required.

Venting can be provided at any location between compressor 60 (if present, then dwell chamber 80), and the outlet of recuperator 40. If the inlet to the compressor 60 is above ambient pressure, venting can also be accomplished at the inlet to compressor 60, further improving system efficiency by not compressing the vent flow in compressor 60. Of course it is understood that venting of any flow prior to entry of the flow into compressor 60 will be vented outside the area intended to be decontaminated by the inventive system. As stated above, bypassing fluid flow 100 around recuperator hot pass 110 can be used to increase the output flow 150 temperature. Venting and/or bypass of fluid flows as described herein can thus be used to selectively and precisely control the final temperature of the treated feed gas stream.

The embodiment of the invention in FIG. 1 provides decontaminated fluid at a temperature above that of initial feed fluid 10. The feed fluid 10, if it is air or a gas mixture that humans can breathe in conditioned spaces occupied by humans, can consist only of air taken from the conditioned space, or it can include a portion of gas taken from a source outside the conditioned space such as outside air or from an other source of breathable gases. Targeted chemical species in other gas flows can be changed especially from dangerous or undesirable species to desirable or benign species at different and possibly higher and lower treatment and/or input and output flow temperatures.

Since fluid stream 10 is heated by recuperator and/or heater 50 before input into compressor 60, one possible embodiment of the present invention provides for compressor 60 to be operated at pressure ratios below 2.0, and preferably of pressure ratios between 1.0 and 1.2, and still more preferably pressure ratios between 1.02 and 1.08. Pressure ratio is defined herein as the compressor stage outlet pressure divided by the compressor stage inlet pressure or $P_o/P_i$.

As discussed above, any compressor type can be employed as the compressor 60. Preferred are compressor types that do not have a built-in volume ratio, such as a Roots-type compressor or a centrifugal compressor that match and adjust to variations in discharge/outlet pressure without throttling. Scroll compressors may be advantageous in low-flow systems. At very low pressure ratios, compressor 60 can be a high pressure fan operating alone or with a continuously or intermittently operating heater 50.

Figure 2:
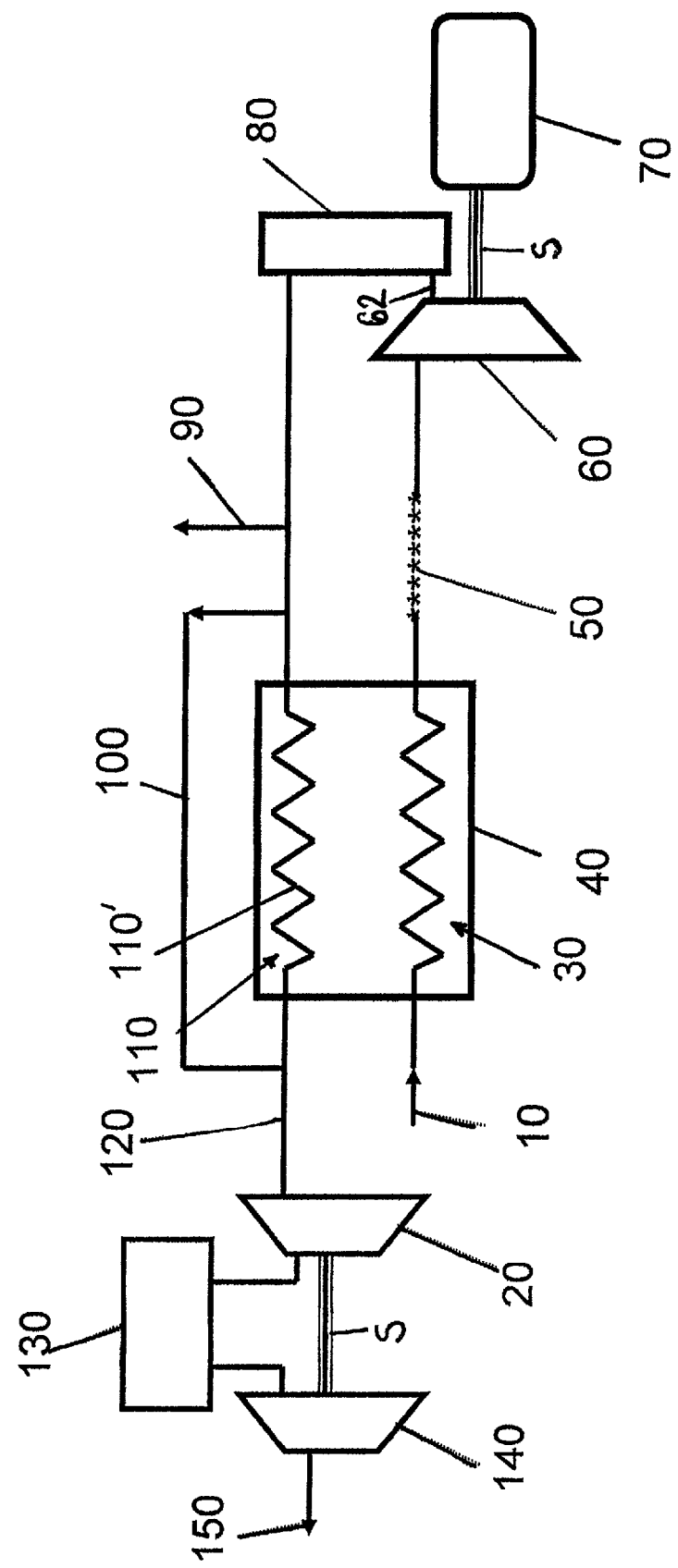

FIG. 2 depicts an embodiment of the invention in which an air cycle cooling process is added to the numbered elements of the embodiment schematically depicted in FIG. 1. Specifically referring to the numbered elements of FIG. 2, fluid stream 120 is compressed in a secondary compressor 20, cooled through heat exchanger 130, and expanded through expander 140. Any expander type can be employed as expander 140, for example, an axial, radial, positive displacement, Roots-type, turbine or scroll expander. Preferred are expander types that provide the maximum efficiency for the pressure ratio and flow of a particular application. The power produced in expander 140 may be used to drive compressor 20 as indicated by drive shaft "S". The pressure of stream 120 entering compressor 20 may be as much as twice the pressure of stream 150 leaving expander 140.

Other cooling systems known to the skilled artisan can be used in place of the air cooling cycle represented by FIG. 2.

Figure 3:
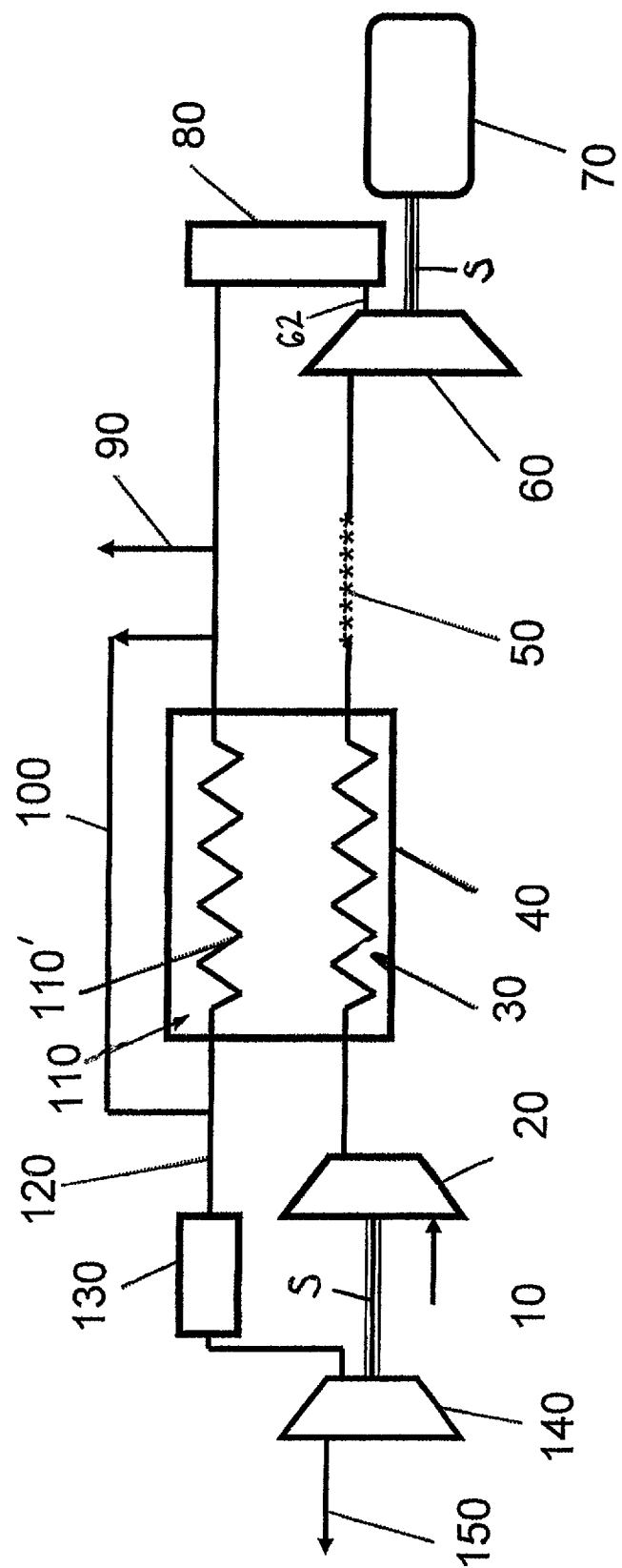

FIG. 3 illustrates yet another embodiment of the invention that may be particularly advantageous when the temperature of the treated fluid flow 150 is desired to be above or below the temperature of inlet fluid feed stream 10, and minimum power is desired to operate the system. In this embodiment, the power from expander 140 is used to drive the compressor 10 via a drive shaft "S", and the temperature of the treated fluid stream may also be controlled. The numbered elements of FIG. 3 correspond to those of FIGS. 1 and 2 for common elements, and these common elements and their function will not again be described in detail. Replacement or substitution of elements in this embodiment may be made as previously stated for FIG. 1, unless otherwise noted, with the same substitutions applying to the embodiments of FIG. 2 and FIG. 4 as well, unless otherwise noted.

Referring to FIG. 3, fluid feed stream 10 is compressed in compressor 20 and heated by passage through cold pass 30 of recuperator 40, and the resulting heated compressed stream is passed through optional heater 50, and then fed to compressor 60, which is driven by a drive shaft "S" and power source 70. The compressed fluid stream at elevated temperature passes from compressor 60 into optional residence chamber 80, allowing the fluid stream to remain for some period of time at elevated temperature. As stated above, this residence chamber 80 may alternately comprise a catalytic converter containing a catalyst that promotes destruction of pathogens or chemical species more quickly or at a lower temperature.

The fluid stream from residence chamber 80 can be divided into up to at least three flow portions: an optional bypass flow portion 100 that bypasses hot pass 110 of recuperator 40, a hot pass flow portion that passes through the hot pass 110 of recuperator 40 and, optionally, a vented flow portion 90 that may be vented from the system.

The hot pass flow portion 110' is cooled by passing through hot pass 110 of recuperator 40 due to heat transfer to cold pass 30. Upon leaving recuperator 40, hot pass flow portion 110' is recombined with bypass flow portion 100 and passes through a heat exchanger 130 where heat may be rejected to the surroundings. The further cooled fluid leaving heat exchanger 130 is directed through and expanded by an expander 140 which further reduces the fluid stream 150 to the desired pressure and temperature. In the case where the feed fluid stream 10 is air, the treated and output air stream may be reduced to a temperature at which it may pass into a conditioned space and, if desired, closely match the heating or cooling load of the conditioned space. In the embodiment shown in FIG. 3, the power produced by expander 140 can be used to drive secondary compressor 20 as indicated by drive shaft "S".

Figure 4:
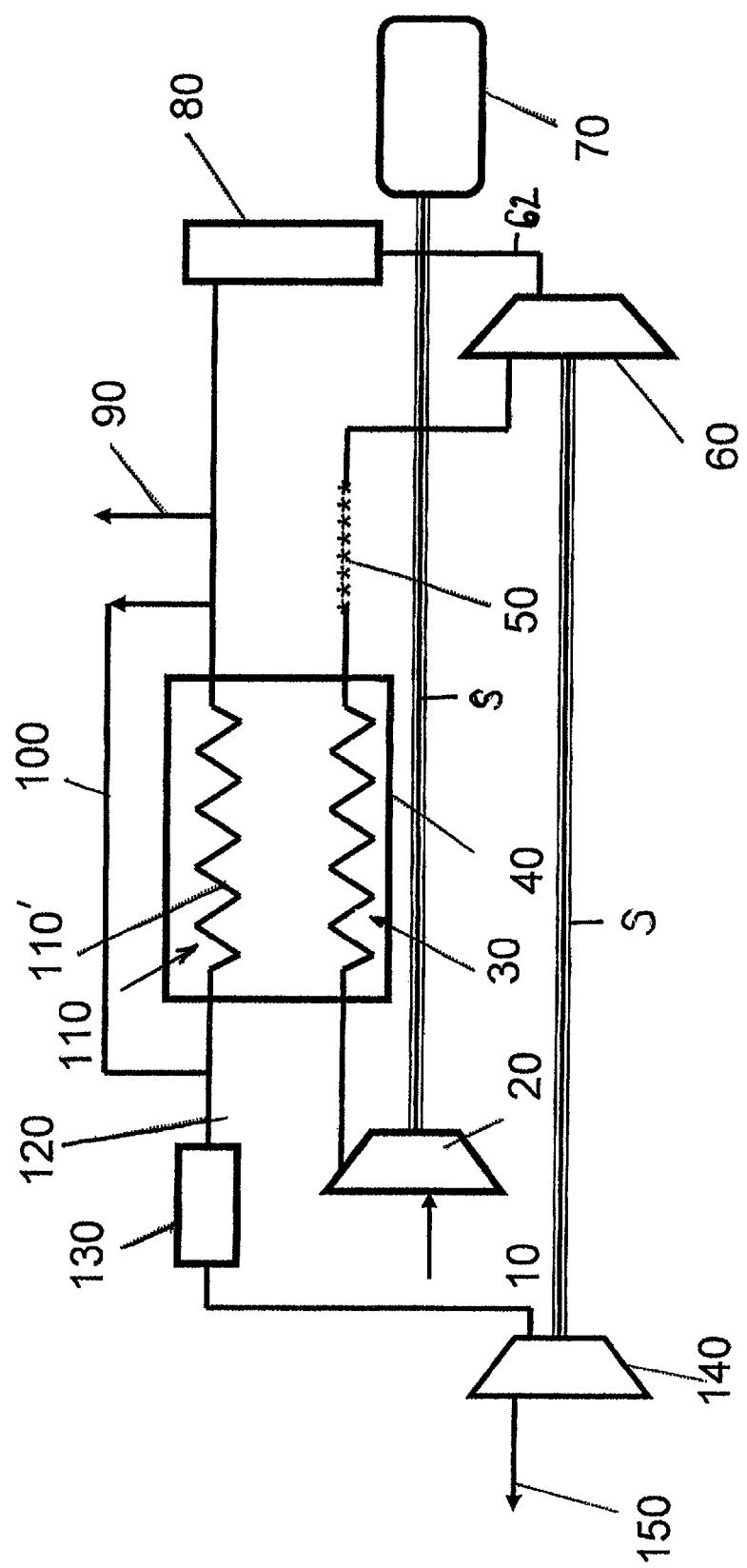

FIG. 4 depicts a further embodiment of the invention that uses all the components of FIG. 3; however, the compressors are connected to different power sources. In this embodiment, as with that illustrated by FIG. 3, expansion power is used to drive the compressor, and the temperature of a fluid stream after destroying or altering of biological and/or chemical species may be further controlled The component numbering of the embodiment of FIG. 4 corresponds to the component numbering of the embodiment of FIGS. 1-3 for common elements, and these common elements and their function will not again be described in detail. In the embodiment depicted in FIG. 4, the power produced by expander 140 is used to drive compressor 60, and the power source 70 is used to drive compressor 20 via drive shafts "S".

To illustrate the invention and the advantages available thereby, a computer simulation of the embodiment of the present invention depicted schematically in FIG. 2 was performed. In this simulation, the fluid feed stream was air, compressors 20 and 60 were assumed to have an efficiency of 70%, and the expander 140 was assumed to have an efficiency of 70%. The recuperator 40 used was a counter-flow device with an effectiveness of 95%. 0% of the feed gas flow was vented, and none of the flow bypassed recuperator hot pass 110.

The results of the example and comparative example are shown in TABLE 1, where column A refers to the invention, and column B refers to simple heating of the fluid feed stream to treatment temperature with a compressor operating at a pressure ratio high enough to reach the required treatment temperature. As can be seen from the results presented in TABLE 1, the example of the invention operates with a power input to the compressor of only 5% of that required by a system using a compressor alone to reach treatment temperature.

TABLE 1

|  | A<br>Invention<br>Embodiment<br>of FIG. 2 | B<br>Comparison<br>Compressive<br>heating |
|---|---|---|
| Inlet Temperature, ° C. | 21 | 21 |
| Treatment Temperature, ° C. | 250 | 250 |
| System Exit Temperature, ° C. | 21 | 250 |
| Compression Ratio |  |  |
| Compressor 60 | 1.033 | — |
| Compressive Heating Compressor | — | 2.55 |
| Machine Efficiencies |  |  |
| Compressor 60 | 0.7 | — |
| Compressor 20 | 0.7 | — |
| Turbine 140 | 0.7 | — |
| Heat Exchanger Effectiveness Ratio |  |  |
| Recuperator 40 | 0.95 | — |
| Rejection Heat Exchanger 130 | 0.7 | — |
| Compressive Heating, kJ/kg | — | 129.6 |
| Compressor Power, kJ/kg | 6.48 | — |
| Relative Power Input to Compressor | 5% | 100% |

Although the invention has been described in detail with reference to certain embodiments, those skilled in the art will recognize that there are other embodiments of the invention within the spirit and scope of the claims.

What is claimed is:

1. A system for purifying a gaseous feed fluid stream by reducing biological and/or chemical particulate contaminants entrained within a said gaseous feed fluid stream, comprising:
   a) at least one recuperator for receiving from a source said gaseous feed fluid stream with said biological and/or chemical contaminants entrained therein, said recuperator comprising a cold pass and a hot pass, wherein said contaminated gaseous feed fluid stream with said biological and/or chemical contaminants entrained therein is introduced into said cold pass;
   b) a compressor for receiving said gaseous feed fluid stream with said biological and/or chemical contaminants entrained therein from said cold pass of said recuperator, said compressor operable to compress said gaseous fluid stream to an elevated pressure and thereby heat said gaseous fluid stream to an elevated temperature sufficient to destroy and/or alter said biological and/or chemical contaminants entrained within said gaseous feed fluid stream resulting in a compressed purified gaseous feed fluid stream; and
   c) passing at least a portion of said compressed purified gaseous fluid stream from said compressor through said hot pass of said recuperator while maintaining said elevated temperature as said compressed purified gaseous fluid stream enters said hot pass and thereby causing heat to be transferred from said compressed purified gaseous feed fluid stream to said gaseous feed fluid stream with said biological and/or chemical contaminants entrained therein passing through said cold pass.

2. The system of claim 1 and further comprising:

a heater for heating said gaseous feed fluid stream exiting said cold pass.

3. The system of claim 1 and further comprising:

a residence chamber for receiving said compressed and heated gaseous fluid stream from said compressor.

4. The system of claim 3 and further comprising:

a conduit for transmitting at least a portion of said compressed and heated gaseous fluid stream from said compressor or said residence chamber through said hot pass of said recuperator.

5. The system of claim 3 wherein said residence chamber contains a catalyst.

6. The system of claim 1 wherein said recuperator is a counter-flow recuperator.

7. The system of claim 1 wherein said elevated pressure comprises a pressure ratio below 2.0.

8. The system of claim 7 wherein said pressure ratio is from 1.02 to 1.08.

9. The system of claim 1 wherein said elevated temperature is from about 200° C. to about 300° C.

10. The system of claim 1 wherein said contaminant is a biological contaminant comprising a bacterial pathogen.

11. The system of claim 1 wherein said compressor is selected from the group consisting of a positive-displacement compressor, a centrifugal compressor, a high pressure centrifugal fan, and combinations thereof.

12. The system of claim 11 wherein said compressor is a Roots positive-displacement compressor.

13. The system of claim 1 and further comprising:

a secondary compressor for receiving a gaseous fluid stream from said hot pass of said recuperator.

14. The system of claim 13 and further comprising:

a heat exchanger for receiving a gaseous fluid stream from said secondary compressor.

15. The system of claim 14 and further comprising:

an expander for receiving a gaseous fluid stream from said heat exchanger.

16. The system of claim 13 wherein said secondary compressor is selected from the group consisting of a positive-displacement compressor, a centrifugal compressor, a high pressure centrifugal fan, and combinations thereof.

17. The system of claim 15 wherein said expander is selected from the group consisting of an axial, radial, positive displacement, Roots, turbine or scroll expander.

18. The system of claim 15 wherein power is transmitted from said expander to said compressor or to said secondary compressor.

* * * * *